United States Patent [19]

Imori et al.

[11] Patent Number: 5,284,977

[45] Date of Patent: Feb. 8, 1994

[54] PROCESS FOR PRODUCING HIGH-PURITY ORGANIC PHOSPHINE

[75] Inventors: Toru Imori; Takayuki Ninomiya; Kazuhiro Kondoh; Kouichi Nakamura; Kouhei Ushikubo, all of Toda, Japan

[73] Assignee: Nippon Mining Company Limited, Tokyo, Japan

[21] Appl. No.: 874,696

[22] Filed: Apr. 28, 1992

[30] Foreign Application Priority Data

Apr. 30, 1991 [JP] Japan .................................. 3-126640
Jun. 5, 1991 [JP] Japan .................................. 3-159866
Jun. 12, 1991 [JP] Japan .................................. 3-166257
Oct. 29, 1991 [JP] Japan .................................. 3-308307

[51] Int. Cl.$^5$ .............................................. C07F 9/02
[52] U.S. Cl. ........................................ 568/8; 568/17
[58] Field of Search ................................... 568/8, 17

[56] References Cited

U.S. PATENT DOCUMENTS 4,113,783  9/1978  Malpass et al. ..................... 568/17
5,041,676  8/1991  Hofmann ............................. 568/8

FOREIGN PATENT DOCUMENTS 2-265588  10/1990  Japan .

OTHER PUBLICATIONS

"High-Purity InP Layer Grown by Metalorganic Chemical Vapor Deposition Using Tertiarybutylphosphine", T. Imori et al., *Appl. Phys. Lett.*, vol. 59, No. 22, Nov.25, 1991, pp. 2862-2864.
C. H. Chen et al., "MOVPE Growth of InP Using Isobutylphosphine and tert-Butylphosphine", Journal of Crystal Growth, 77 (1986), pp. 11-18.

Primary Examiner—Marianne M. Cintins
Assistant Examiner—Margaret J. Page
Attorney, Agent, or Firm—Webb, Burden, Ziesenheim & Webb

[57] ABSTRACT

A high-purity organic phosphine is obtained by washing organic phosphine or an organic solvent solution thereof with water, an alkaline aqueous solution or an acidic aqueous solution, whereby impurities, particularly, silicon compounds, 2-methoxy ethanol, and organic halides, contained in organic phosphine can be removed, so that such high-purity organic phosphine may be used as a raw material for high-performance compound semiconductor thin film with Groups III and V elements of the Periodic Table.

13 Claims, No Drawings

PROCESS FOR PRODUCING HIGH-PURITY ORGANIC PHOSPHINE

BACKGROUND OF THE INVENTION (1) Field of the Invention

The present invention relates to a process for producing high-purity organic phosphines. Particularly, the present invention relates to a process for producing high-purity organic phosphines usable as a raw material in the formation of compound semiconductor thin film by the Metal Organic Chemical Vapor Deposition Method (MOCVD).

(2) Description of the Prior Art

Compound semiconductor films formed with compounds of elements in Groups III and V of the periodic table, such as indium and phosphorus, are useful as materials in the manufacture of electronic devices. There are available for forming the compound semiconductor thin film such methods as (1) Molecular beam epitaxy (MBE), (2) halide CVD, (3) metal organic Chemical Vapor Deposition (MOCVD), and (4) metal organic molecular beam epitaxy (MOMBE), etc. Of these said methods, MOCVD and MOMBE have come into wide use and attracted attention of concerned circles, since said two methods do not require high vacuum within the crystal growth system, thus readily permitting exchange of raw materials.

However, in case either one of the aforementioned methods is employed to produce compound semiconductors consisting of elements in Group III of the Periodic Table and phosphorus, which use phosphine, a highly toxic phosphorus hydride compound, as the raw material. Needless to say, the use of phosphine in substantial quantities in mass production of semiconductors is inevitably accompanied by grave concerns about environmental as well as workshop safety.

Recently, proposals have been made, with the said potential hazard in view, to use organic phosphines, such as alkyl phosphine and aryl phosphine in place of phosphine. Among those organic phosphines, in particular, monoalkyl or monoaryl phosphine are being looked upon as promising low-toxicity substitute materials for phosphine, since monoalkyl phosphine and monoaryl phosphine cause only little carbon contamination into the semiconductor thin film (e.g. J. Crystal Growth, 77 (1986) 11-18).

Among those well-known processes for producing the aforementioned organic phosphines, the following may be cited as representative examples.

(1) Reduction of an organic halogenophosphorus compound with lithium aluminum hydride or sodium.

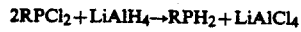

(2) Reduction of diester of organic phosphonous acid or diester of organic phosphonic acid by lithium aluminum hydride

(3) Reaction of phosphine with olefin

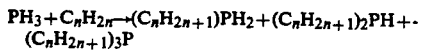

(see "Shin Jikken Kagaku Koza" (A Series of Courses on New Experimental Chemistry) Vol.12, p. 421, published by Maruzen Co., Ltd., Tokyo, in 1976).

Out of these processes for synthesizing organic phosphines, in the cases of the reduction processes such as (1) and (2) as set forth above, it is known to be advantageous from the viewpoint of improving the yield to use as the reducing agent principally a compound having active hydride in its molecule, such as lithium aluminum hydride and sodium borohydride ($NaBH_4$). However, the inventors of the present invention have discovered that the use of sodium bis(2-methoxyethoxy) aluminum hydride ($NaAlH_2(OC_2H_4OCH_3)_2$) is effective for preventing contamination of organic phosphine with organic halide and/or other impurities, and hence proposed a process for producing high-purity alkyl phosphines (Japanese Patent Application Hei-2-265588).

Although sodium bis (2-methoxyethoxy) aluminum hydride is an effective reducing agent as proposed, the use thereof has posed a problem in that 2-methoxy ethanol, derived from the reducing agent, contaminates the organic phosphine.

What is more, in such reduction reaction using either one of the aforementioned reducing agents, complex intermediate compounds are formed. An acid such as hydrochloric acid is used to hydrolyze these complex intermediate compounds.

In a step of said hydrolysis process, a part of organic phosphines produced by the reduction are decomposed, whereby organic halides, such as alkyl halides and aryl halides, are produced.

Furthermore, an alkyl halide or an aryl halide which is used as the alkyl source or aryl source in the synthesis of an organic halogenophosphorus compound or an oxoacid ester of phosphorus is often entrained in the organic halogenophosphorus compound or an oxoacid ester of phosphorus and remains in the alkyl phosphine or aryl phosphine. Generally, separation purification by distillation, etc. has been hardly practicable, since the boiling points of alkyl phosphine or aryl phosphine and alkyl halide or aryl halide are close to each other.

In as much as the semiconductor manufacture requires particularly high-purity organic phosphines, it has been a requisite condition that trace contents of impurities, particularly, silicon, organic halides and 2-methoxy ethanol, be removed from the reduction product.

SUMMARY OF THE INVENTION

The present invention has resolved the aforementioned problem. Specifically, it is the object of the present invention to provide a process for obtaining high-purity organic phosphines wherefrom trace contents of impurities, particularly silicon, organic halides, 2-methoxy ethanol and the like, are removed to a far extent.

That is to say, the present invention comprises washing an organic phosphine or an organic solvent solution thereof with water, an alkaline aqueous solution or an acidic aqueous solution. In a particularly preferable mode of operation, the present invention comprises a process for producing high-purity organic phosphines, wherein the aforementioned organic phosphine is an alkyl phosphine or an aryl phosphine, these organic phosphines being obtained by first reducing an organic halogenophosphorus compound or an oxoacid ester of phosphorus with a reducing agent containing an active hydride in its molecule and then hydrolyzing the thus obtained reduction product, the said oxoacid ester of phosphorus being selected from a group consisting of diester of organic phosphonous acid, diester of organic phosphonic acid, ester of organic phosphinous acid or ester of organic phosphinic acid, and the said hydrolysis being performed with addition of neutral water.

DESCRIPTION OF THE PREFERRED EMBODIMENT

The present invention may be applied to various kinds of organic phosphine. Of these organic phosphines, preferred organic phosphines are such organic phosphines as monoalkyl or monoaryl phosphines, or dialkyl or diaryl phosphines, or trialkyl or triaryl phosphines having a substituent group such as isopropyl, tert-butyl or phenyl groups that can be used as raw material in the preparation of compound semiconductor thin film by MOCVD and the like.

Preferable examples of these organic phosphines are those which are obtained by (i) reducing organic dihalogenophosphorus compound such as phosphonous acid dihalides ($RPX_2$), and phosphonyl dihalides ($RP(O)X_2$), organic monohalogenophosphorus compound such as phosphinous acid halides ($R_2PX$) or phosphinyl halide ($R_2P(O)X$), or oxoacid ester of phosphorus, such as diester of phosphonous acid ($RP(OR')_2$), diester of phosphonic acid ($RP(O)(OR')_2$), ester of phosphinous acid ($R_2P(OR')$), ester of phosphinic acid ($R_2P(O)(OR')$) by a reducing agent having an active hydride in its molecule, such as sodium bis(2-methoxy ethoxy) aluminum hydride, lithium aluminum hydride, and sodium borohydride, and (ii) hydrolyzing the product of said reduction.

Of said compounds, wherein R consists of monoalkyl or monoaryl group such as isopropyl, tert-butyl or phenyl groups, are particularly preferable. In said reduction step, use of sodium bis(2-methoxyethoxy) aluminum hydride or lithium aluminum hydride is particularly preferable, since such use reduces the amount of organic halides contaminating the end product as impurities.

Furthermore, although the conventional process for hydrolysing depends on use of an acid, in the production of high-purity organic phosphines, as is the case with the present invention, a neutral water, such as pure water, having a pH of 6 to 8, more preferably 6.5 to 7.5, is preferably used, since use of such water serves to reduce the amount of silicon entrained as an impurity in the end product. In the said case, the amount of water added for the hydrolysis is preferably in an amount at least sufficient to bring the yield to the saturated point, preferably within such limit that will be suitable for the reaction system, in consideration of the increase in size of the reactor vessel in consequence of the increase of the volume of water added. It is necessary to make a provision for regulating the rate of dropping of water to prevent "uncontrollable reaction", since a large amount of gas is generated in the initial stage of hydrolysis.

According to the present invention, organic phosphine particularly preferably such organic phosphine that is obtained by the aforementioned method is washed with water, an alkaline aqueous solution or an acidic aqueous solution. The kind of the washing water is selected in accordance with the type of impurities to be removed. In cases where silicon compounds are included as impurities, it is preferable that the washing is performed with an alkaline aqueous solution, for which potassium hydroxide or sodium hydroxide may be used as alkali. The alkali concentration is preferably 3 normal or lower, although it should be varied with the amount of organic phosphine to be treated. It is preferable that the duration and frequency of washing be determined at adequate levels while monitoring the amount of entrained silicon. Although it is preferable that the washing be carried out at a temperature in the range of from room temperature to 100° C., the room temperature is generally sufficient. The amount of alkaline aqueous solution to the amount of organic phosphine is preferably in the range of 10 to 50% by weight per unit weight of organic phosphine, while an optimum amount depends on the amount of contained silicon compound. If the amount of such alkaline aqueous solution is less than said amount, the effect of removal is insufficient. If the amount is excessively large, a disadvantage arises such that the amount of lost organic phosphine increases. By washing organic phosphine with alkaline aqueous solution, the silicon content in the organic phosphine can be reduced to 0.03 ppm or less.

On the other hand, in cases where 2-methoxy ethanol is entrained as an impurity, it suffices to use water or an acidic water for the washing; and if water is used, water having a pH in the range of 6 to 8, particularly in the range of 6.5 to 7.5.is preferable. While a mineral acid or an organic acid may be used to prepare an acidic water, the use of hydrochloric acid, sulfuric acid, etc. is convenient as well as preferable. Although there is no limitation to the acid concentration, the use of a dilute acid is economical and preferable. If the liquid is alkaline, there is not imparted by such liquid virtually any effect of reducing 2-methoxy ethanol. While the amount of such water or acidic aqueous solution used for said purpose may be varied according to the amount of the entrained 2-methoxy ethanol, it suffices to use water in an amount approximately equivalent to that of the organic phosphine in case where the amount of the said impurities are in the order of 1000 ppm. If the amount of the washing liquid exceeds the said level, the yield decreases, and if it is less, the effect of reducing 2-methoxy ethanol decreases.

In cases where organic halides are entrained as impurities, those organic halides can be removed by using an aqueous solution of sulfuric acid. But organic halides cannot be removed by washing with an aqueous solution of hydrochloric acid. While there is no particular limitation to the sulfuric acid concentration, it is more economical to use a dilute acid, and hence it is preferable to select an adequate concentration in the range of 0.5 to 5N. As for the amount of aqueous solution of sulfuric acid, it suffices to use a solution of 2N sulfuric acid in an amount approximately equivalent to that of organic phosphine in case organic halides are entrained in the order of 1000 ppm, while an optimum amount of aqueous solution of sulfuric acid depends on the amount of organic halides present.

Although washing with the aforementioned water, alkaline aqueous solution or acidic aqueous solution may be carried out individually according to the intended effect, the washing may be performed consecutively, using two or three kinds of washing process in an adequately selected combination.

Although the aforementioned washing may be carried out on organic phosphine as it is, it is preferable that washing be carried out with the organic phosphine dissolved in an organic solvent having a high separability from water and a low reactivity with organic phosphines. There can be cited as examples of such solvent ethers such as di-n-butyl ether, diisopentyl ether, and the like. The amount of organic solvent in the said case is preferably in the range of 10 to 50% by weight as the organic phosphine concentration, while such amount depends on the amount of impurities and the kind of the organic solvent to be used.

The washed material is preferably rectified by distillation, while any kind of distilling method may be adopted. It is particularly preferable to purify by repeated distillation to obtain high-purity organic phosphine suitable as a raw material for semiconductor.

EXAMPLES

The invention is now illustrated with reference to the following examples. The recited operations were carried in inert atmosphere in all cases.

EXAMPLE 1

347 g of a sodium bis(2-methoxyethoxy) aluminum hydride in 70% toluene solution was measured into a flask, and toluene therein contained was distilled out by reduced pressure distillation under the conditions of a temperature of 100° C., a pressure of 5 mmHg in 3 hours. After allowing the flask to cool off, 70 g of tert-butyldichlorophosphonyl (tert-BuP(O)Cl$_2$) dissolved in 200 ml of di-n-butyl ether, was dropped into sodium bis(2-methoxyethoxy) aluminum hydride cooled to about −10° C. After the whole amount of tert-butyldichloro-phosphonyl was dropped, the liquid was maintained for 1 hour at about 60° C. with agitation. Then, after cooling off the liquid to room temperature, it was once again cooled down to about −10° C., whereupon 900 ml of water was gradually added to it. The reaction liquid first became turbid with a milky color and with a further continued addition of water the liquid was separated into two phases. By distilling the organic phase as the upper phase fluid, 18 g of a colorless and transparent fluid was obtained (the yield being 50%). By a quantitative analysis of the fluid by the Inductive Coupled Plasma Method (ICP), the silicon content was determined to be 0.2 ppm. By rectifying the fluid the silicon content was reduced to 0.03 ppm, the lower limit of detectable silicon content by ICP, or less.

Using the obtained tert-butylphosphine and commercially available trimethyl indium, an InP epitaxial thin film was caused to grow at atmospheric pressure on an InP substrate which was placed in a horizontal MOCVD system (Nippon Sanso K.K. HR-1124) at a growth temperature of 600° C. and a Group V/Group III ratio of 30. By measuring the electrical properties of the obtained thin film by the Van der Pauw method, the following values were obtained.

Mobility $\mu_{77k}$ = 50,500 cm$^2$/v.sec

Carrier concentration $N_{77k}$ = 1.7 × 10$^{15}$ cm$^{-3}$

COMPARATIVE EXAMPLE 1

357 g of a sodium bis(2-methoxyethoxy) aluminum hydride in 70% toluene solution was caused to react with 72 g of tert-butyldichlorophosphonyl (t-BuP(O)Cl$_2$) in the same procedure as in Example 1, and after the reaction was completed, hydrolysis was carried out by adding 900 ml of an aqueous solution of 6N hydrochloric acid in place of water. Then, by distilling the organic phase, 21 g of a colorless and transparent fluid was obtained (the yield being 56%). The silicon content of the obtained liquid was determined to be 0.7 ppm by ICP. By rectifying the fluid, the silicon content was 0.7 ppm.

As the result of measurement of the electrical properties of the InP epitaxial thin film produced in an MOCVD system, using the obtained tert-butylphosphine and commercially available trimethyl indium, according to the same procedure as in Example 1, the following values were obtained.

Mobility $\mu_{77k}$ = 7,900 cm$^2$/v.sec

Carrier concentration $N_{77k}$ = 2.3 × 10$^{16}$ cm$^{-3}$

The product thus obtain did not give any sufficient electrical properties, compared with the one obtained by the hydrolysis with water.

EXAMPLE 2

100 ml of di-n-butyl ether was added to 80 g of tert-butylphosphine containing 0.4 ppm of silicon, and further 100 ml of aqueous solution of 2N potassium hydroxide was added. This mixture was intensively agitated for 50 hours at room temperature. After the agitation, the organic phase was rectified, whereby 56 g of a colorless and transparent fluid was obtained. By ICP the silicon content of the fluid was found to be 0.03 ppm or less, which is the detectable lower limit.

As the result of measurement of the electrical properties of the InP epitaxial thin film produced in an MOCVD system, using the obtained tert-butylphosphine and commercially available trimethyl indium, according to the same procedure as in Example 1, the following values were obtained.

Mobility $\mu_{77k}$ = 105,000 cm$^2$/v.sec

Carrier concentration $N_{77k}$ = 3.3 × 10$^{14}$ cm$^{-3}$

The above-mentioned values are sufficient as those for semiconductor.

EXAMPLE 3

100 ml of di-n-butyl ether was added to 50 g of tert-butylphosphine containing 0.2 ppm of silicon, and further 100 ml of aqueous solution of 2N sodium hydroxide was added to the mixture. This final mixture was intensively agitated for 3 hours at room temperature. 31 g of a colorless and transparent fluid obtained by rectification which was carried out in the same procedure as in Example 1 gave a silicon content of 0.03 ppm or less, which is the detectable lower limit.

EXAMPLE 4

15 g of pure water was added to 10 g (14 ml) of tert-butylphosphine containing 1,500 ppm of 2-methoxy ethanol. After agitating this mixture for 30 minutes, the fluid was separated into two phases, the upper phase being tert-butylphosphine. The upper phase was extracted and subjected to a quantitative analysis by gas chromatography for 2-methoxy ethanol. The 2-methoxy ethanol content was determined to be less than the detectable lower limit by gas chromatography (10 ppm or less).

EXAMPLE 5

The same procedure was followed as in Example 4 except that aqueous solution of 2N hydrochloric acid was used in place of pure water. The obtained fluid exhibited a 2-methoxy ethanol content of 10 ppm or less.

EXAMPLE 6

The same procedure was followed as in Example 4 except that aqueous solution of 2N sulfuric acid was used in place of pure water. The obtained fluid exhibited a 2-methoxy ethanol content of 10 ppm or less.

COMPARATIVE EXAMPLE 2

Tert-butylphosphine containing 1,500 ppm of 2-methoxy ethanol was rectified by a 50 centimeter-long distillation column. The 2-methoxy ethanol was decreased to 700 ppm in the principal fraction. After 4 repeated steps of distillation, the 2-methoxy ethanol content in the principal fraction became 200 ppm.

EXAMPLE 7

20 g of tert-butylphosphine containing 300 ppm of tert-butyl chloride was diluted with 30 ml of di-n-butyl ether. The obtained mixture was added with 30 ml of 2N sulfuric acid, whereupon the fluid thus obtained was agitated for 1 hour. The fluid underwent a phase separation after it was left to stand. The ether phase was washed twice with water and then distilled at atmospheric pressure by a 50 centimeter-long distillation column. The tert-butyl chloride content in the obtained fraction was lower than the detectable lower limit (about 10 ppm) by gas chromatography.

COMPARATIVE EXAMPLE 3

20 g of tert-butylphosphine containing 300 ppm of tert-butyl chloride was distilled by a 50 centimeter-long distillation column. The tert-butyl chloride content in the obtained fraction was 220 ppm, which represents only a slight decrease.

We claim:

1. A process for producing high-purity organic phosphines, which comprises washing at least one organic phosphine or an organic solvent solution of at least one organic phosphine with an alkaline aqueous solution to remove any silicon compounds which may be present with said organic phosphine.

2. A process for producing high-purity organic phosphines, which comprises washing at least one organic phosphine or an organic solvent solution of at least one organic phosphine with water or an acidic aqueous solution to remove any 2-methoxy ethanol which may be present with said organic phosphine.

3. A process for producing high-purity organic phosphines, which comprises washing at least one organic phosphine or an organic solvent solution of at least one organic phosphine with an aqueous solution of sulfuric acid to remove any organic halides which may be present with said organic phosphine.

4. A process for producing high-purity organic phosphines according to claim 1, wherein said organic phosphine is an alkyl phosphine.

5. A process for producing high-purity organic phosphines according to claim 2, wherein said organic phosphine is a product obtained by reducing either an organic halogenophosphorus or an oxoacid ester of phosphorus by a reducing agent having an active hydride in its molecule to a reduced product and hydrolyzing said reduced product by adding neutral water.

6. A process for producing high-purity organic phosphines according to claim 5, wherein said oxoacid ester of phosphorus is selected from the group consisting of diester of organic phosphonous acid, diester of organic phosphonic acid, ester of organic phosphinous acid, and ester of organic phosphinic acid.

7. A process for producing high-purity organic phosphines according to claim 5, wherein said reducing agent is sodium bis(2-methoxyethoxy) aluminum hydride.

8. A process for producing high-purity organic phosphines according to claim 2 wherein said organic phosphine is an alkyl phosphine.

9. A process for producing high-purity organic phosphines according to claim 3 wherein said organic phosphine is an alkyl phosphine.

10. A process for producing high-purity organic phosphines according to claim 1 wherein said organic phosphine is a product obtained by reducing either an organic halogenophosphorus or an oxoacid ester of phosphorus by a reducing agent having an active hydride in its molecule to a reduced product and hydrolyzing said reduced product by adding neutral water.

11. A process for producing high-purity organic phosphines according to claim 3 wherein said organic phosphine is a product obtained by reducing either an organic halogenophosphorus or an oxoacid ester of phosphorus by a reducing agent having an active hydride in its molecule to a reduced product and hydrolyzing said reduced product by adding neutral water.

12. A process for producing high-purity organic phosphines according to claim 10 wherein said oxoacid ester of phosphorus is selected from the group consisting of diester of organic phosphonous acid, diester of organic phosphonic acid, ester of organic phosphinous acid, and ester of organic phosphinic acid.

13. A process for producing high-purity organic phosphine according to claim 11 wherein said oxoacid ester of phosphorus is selected from the group consisting of diester of organic phosphonous acid, diester of organic phosphonic acid, ester of organic phosphinous acid, and ester of organic phosphinic acid.

* * * * *